(12) United States Patent
Johnson et al.

(10) Patent No.: US 7,765,015 B2
(45) Date of Patent: Jul. 27, 2010

(54) LEAD WITH INFLATABLE FIXATION MECHANISM

(75) Inventors: Eric T. Johnson, Temecula, CA (US); Brian D. Soltis, St. Paul, MN (US); Bruce A. Tockman, Scandia, MN (US); Peter J. D'aquanni, Murrieta, CA (US); Kent C. B. Stalker, San Marcos, CA (US); Gayla A. Smith, Sun City, CA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 736 days.

(21) Appl. No.: 11/622,810

(22) Filed: Jan. 12, 2007

(65) Prior Publication Data

US 2008/0172118 A1 Jul. 17, 2008

(51) Int. Cl.
*A61N 1/05* (2006.01)
(52) U.S. Cl. ...................................... 607/126; 607/122
(58) Field of Classification Search ........................ None
See application file for complete search history.

(56) References Cited

U.S. PATENT DOCUMENTS

| | | | |
|---|---|---|---|
| 3,937,225 A | 2/1976 | Schramm | |
| 4,519,403 A | 5/1985 | Dickhudt | |
| 4,531,943 A | 7/1985 | Van Tassel et al. | |
| 4,551,292 A | 11/1985 | Fletcher et al. | |
| 4,559,951 A | 12/1985 | Dahl et al. | |
| 4,706,682 A | 11/1987 | Stypulkowski et al. | |
| 4,863,442 A | 9/1989 | De Mello et al. | |
| 5,025,786 A | 6/1991 | Siegel | |
| 5,087,244 A | 2/1992 | Wolinsky et al. | |
| 5,282,785 A | 2/1994 | Shapland et al. | |
| 5,284,146 A | 2/1994 | Czar et al. | |
| 5,571,159 A | 11/1996 | Alt | |
| 5,855,546 A | 1/1999 | Hastings et al. | |
| 5,925,073 A | 7/1999 | Chastain et al. | |
| 5,951,597 A | 9/1999 | Westlund et al. | |
| 5,991,668 A | 11/1999 | Leinder et al. | |
| 6,136,021 A | 10/2000 | Tockman et al. | |

(Continued)

OTHER PUBLICATIONS

U.S. Appl. No. 11/424,440, filed Jun. 15, 2006; First Named Inventor: Brian Soltis; Title: Lead With Orientation Freature.

(Continued)

*Primary Examiner*—Kennedy J Schaetzle
(74) *Attorney, Agent, or Firm*—Faegre & Benson LLP

(57) ABSTRACT

A medical electrical lead configured for use in stimulating the left side of the heart (i.e., the left ventricle). In one embodiment, the lead includes an elongate lead body including an inner surface. An inflatable member is disposed on the outer surface of the body between its proximal and distal ends, the inflatable member being adapted when inflated to impart a radial force on and frictionally engage a surface of the coronary sinus or coronary vein for fixation of the distal end of the lead therein. The lead further includes a conductive member extending from the proximal end toward the distal end, and an inner insulating layer positioned between the conductive member and the inner surface of the body. Separation between the inner insulating layer and the inner surface of the body defines an inflation lumen in fluid communication with the inflatable member.

19 Claims, 5 Drawing Sheets

U.S. PATENT DOCUMENTS

| | | |
|---|---|---|
| 6,385,492 B1 | 5/2002 | Ollivier et al. |
| 6,510,348 B2 * | 1/2003 | Clemens et al. ............. 607/119 |
| 6,529,779 B1 | 3/2003 | Sutton |
| 6,741,893 B2 | 5/2004 | Smits |
| 7,099,718 B1 | 8/2006 | Thacker et al. |
| 2002/0077685 A1 | 6/2002 | Sundquist et al. |
| 2003/0050681 A1 | 3/2003 | Pianca et al. |
| 2003/0220677 A1 | 11/2003 | Doan et al. |
| 2004/0059404 A1 | 3/2004 | Bjorklund et al. |
| 2004/0230282 A1 | 11/2004 | Cates et al. |
| 2004/0243210 A1 | 12/2004 | Morgan et al. |
| 2005/0113900 A1 | 5/2005 | Shiroff et al. |
| 2006/0089694 A1 | 4/2006 | Zhang et al. |

OTHER PUBLICATIONS

International Search Report and Written Opinion of International application No. PCT/US2008/050455, mailed May 21, 2008, 13 pp.

* cited by examiner

LEAD WITH INFLATABLE FIXATION MECHANISM

TECHNICAL FIELD

The present invention relates to medical devices and methods for accessing an anatomical space of the body. More specifically, the invention relates to devices and methods for securing a lead within a branch of the coronary sinus.

BACKGROUND

Implantable medical devices for treating irregular contractions of the heart with electrical stimuli are known. Exemplary implantable devices are defibrillators and pacemakers. Various types of electrical leads for defibrillators and pacemakers have been suggested, many of which are placed transvenously. Such leads are introduced into the patient's vasculature at a venous access site and travel through veins to the sites where the leads' electrodes will be implanted or otherwise contact target coronary tissue. Electrodes for transvenously-placed leads can be implanted in the endocardium (the tissue lining the inside of the heart) of the right atrium or ventricle, or alternatively, in the branch vessels of the coronary venous system. In particular, lead electrodes can be implanted in the coronary sinus or a branch vessel thereof for sensing and/or stimulating the left side of the heart (i.e., the left ventricle).

Various techniques have been used to facilitate both acute and chronic fixation of the foregoing types of leads at the desired implantation sites. For leads partially implanted within the coronary venous system, fixation techniques should be atraumatic and yet provide fixation sufficient to withstand natural heart motion and retrograde blood flow which naturally tend to push the lead out of the branch vessel into which the electrode is implanted. Additionally, it is desirable for the fixation means to be reversible so as to permit and facilitate partial or complete removal of the lead and fixation structures after implantation if necessary or desired. At the same time, the fixation means should be adaptable for incorporation in small diameter leads (e.g., down to 6 French or 3 French) for use in stimulating the left side of the heart.

Accordingly, there is a continuing need for improved devices and methods for acute and/or chronic fixation of cardiac leads in the coronary venous systems. In particular, there is a need in the art for a fixation approach for small diameter leads that effectively secures the lead electrodes in the target coronary branch vessel.

SUMMARY

The present invention, in one embodiment, is a medical electrical lead comprising an elongate lead body having a proximal end, a distal end, an outer surface, and an inner surface. The body is made from an electrically insulative material and dimensioned such that the distal end can be implanted in a coronary sinus or coronary vein. The lead further comprises an inflatable member disposed on the outer surface of the body between the proximal and distal ends. The inflatable member is adapted to assume a deflated state and an inflated state in which the inflatable member is adapted to impart a radial force on and frictionally engage a surface of the coronary sinus or coronary vein for fixation of the distal end therein. Additionally, the lead comprises a conductive member extending from at least the proximal end toward the distal end of the body, and an electrode on the body electrically coupled to the conductive member. The lead further comprises an inner insulating layer disposed between the conductive member and the inner surface of the body and extending from the proximal end toward the distal end, and an inflation lumen between the inner insulating layer and the inner surface of the body in fluid communication with the inflatable member.

The present invention, in another embodiment, is a medical electrical lead comprising an elongate lead body having a proximal end, a distal end, an outer surface, and an inner surface. The body is made from an electrically insulative material and dimensioned such that the distal end can be implanted in a coronary sinus or coronary vein. The lead further comprises an inflatable member disposed on the outer surface of the body between the proximal and distal ends. The inflatable member is adapted to assume a deflated state and an inflated state in which the inflatable member is adapted to impart a radial force on and frictionally engage a surface of the coronary sinus or coronary vein for fixation of the distal end therein. Additionally, the lead comprises a conductive member extending from at least the proximal end toward the distal end of the body, and an electrode on the body electrically coupled to the conductive member. The conductive member includes an insulative coating, wherein separation between the insulative coating and the inner surface of the body defines an inflation lumen in fluid communication with the inflatable member.

In another embodiment, the present invention is a medical electrical lead comprising an elongate lead body having a proximal end, a distal end, an outer surface, and an inner surface. The body is made from an electrically insulative material and dimensioned such that the distal end can be implanted in a coronary sinus or coronary vein. The lead further comprises an inflatable member disposed on the outer surface of the body between the proximal and distal ends. The inflatable member is adapted to assume a deflated state and an inflated state in which the inflatable member is adapted to impart a radial force on and frictionally engage a surface of the coronary sinus or coronary vein for fixation of the distal end therein. Additionally, the lead comprises a conductive member extending from at least the proximal end toward the distal end of the body, and an electrode on the body electrically coupled to the conductive member. The lead further comprises a generally tubular, flexible sheath made of an electrically insulative material is disposed between the conductive member and the inner surface of the body, wherein separation between the sheath and the inner surface of the body defines an inflation lumen in fluid communication with the inflatable member.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
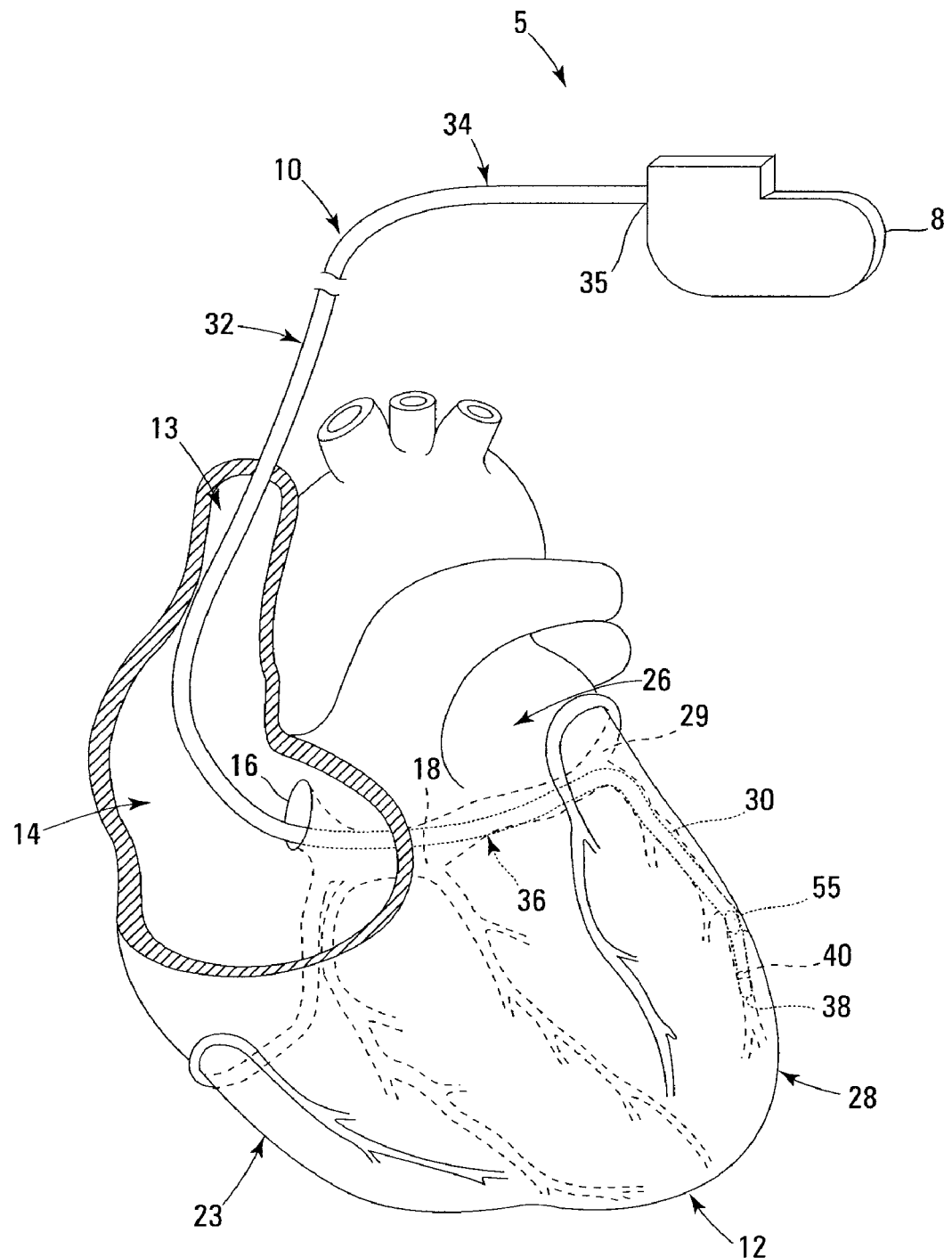
FIG. 1 is a schematic drawing of a cardiac rhythm management system including a pulse generator coupled to a lead deployed in a patient's heart according to one embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic drawing of a cardiac rhythm management system 5 including a pulse generator 8 coupled to a lead 10 deployed and secured in a patient's heart 12 according to one embodiment of the present invention. As shown, the heart 12 includes a superior vena cava 13, a right atrium 14 and a right ventricle 23, a left atrium 26 and a left ventricle 28, a coronary sinus ostium 16 in the right atrium 14, a coronary sinus 18, and various cardiac vessels including a great cardiac vein 29 and other branch vessels off the coronary sinus 18 including an exemplary branch vessel 30.

In the illustrated embodiment, the lead 10 includes an elongate lead body 32 made of an electrically insulative material and having a proximal portion 34 including a proximal end 35, and a distal portion 36 including a distal end 38. The distal portion 36 includes at least one electrode 40. As shown, the proximal end 35 is mechanically and electrically coupled to the pulse generator 8, and the distal portion 36 extends through the superior vena cava 13, the right atrium 14, and the coronary sinus 18, and into the branch vessel 30, with the distal end 38, and thus the electrode 40, positioned within the branch vessel 30. The illustrated position of the lead 10 may be used, for example, for sensing physiologic parameters and delivering a pacing and/or defibrillation stimulus to the left side of the heart 12. In other embodiments, the lead 10 may also be deployed in other coronary vessels such as the great cardiac vein 29 or other branch vessels for providing therapy to the left side (or other portions) of the heart 12.

Additionally, the lead 10 includes a fixation feature in the form of an inflatable member 55 located on the lead body 32 in the distal portion 36. As will be explained in detail below, the inflatable member 55 is operable to assume deflated and inflated states, the latter for use in acutely and/or chronically securing the distal end 38, and in particular, the electrode 40, in the desired implantation location. In the illustrated embodiment, the inflatable member 55 extends entirely circumferentially around the lead body 32. As will be shown and discussed below, in other embodiments, the inflatable fixation member may extend only partially around the lead body and/or may have alternative shapes. In various embodiments, a plurality of inflatable members may be provided at predetermined locations along the length of the lead body 32.

Figure 2A:
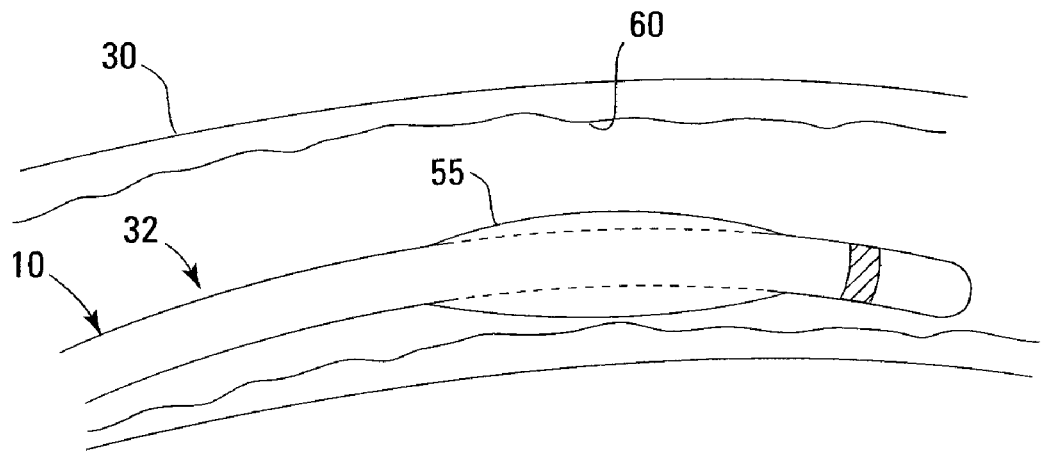
FIGS. 2A and 2B are schematic views of a distal portion of a lead including an inflatable fixation member according to an embodiment of the present invention.
Figure 2B:
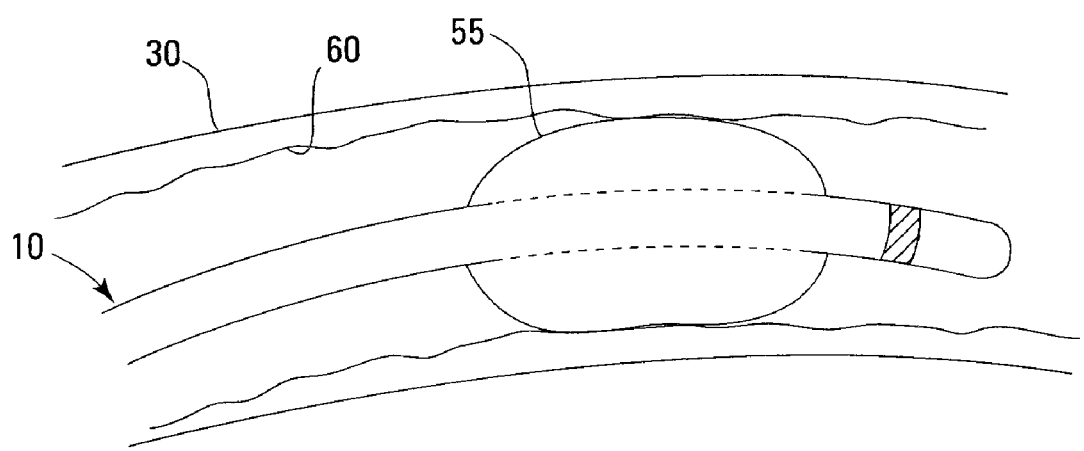

FIGS. 2A and 2B are schematic views of the distal portion 36 of the lead 10 positioned in the branch vessel 30 according to an exemplary embodiment of the present invention. As shown, the inflatable member 55 can assume a deflated state (FIG. 2A) for delivery of the lead 10 to the desired implantation location. In the deflated state, the inflatable member 55 does not appreciably increase the outer diameter of the lead body 32 so as not to appreciably interfere with or impede transvenous delivery of the lead 10. Once positioned, the inflatable member 55 can be inflated so as to expand radially and impart a radial force on an interior surface 60 of the coronary branch vessel 30. The inflatable member 55 may, if desired, be subsequently deflated to remove the fixation force, according to the needs of the clinician. For example, in some embodiments, the clinician may determine that the lead 10 should be re-positioned in the same or different coronary vessel after its initial deployment. Alternatively, deflation of the inflatable member 55 may be effected to facilitate removal of the lead 10 from the patient. In some embodiments, the inflatable member 55 may be used for delivery of the lead only, for example, to provide a temporary fixation and stabilization force during retraction of a guide wire or guide catheter from the patient. Additionally, the degree of fixation (i.e., the magnitude of the radial force imparted on the interior surface 60 by the inflatable member 55) can be adjusted by increasing or decreasing the inflation pressure in the inflatable member 55. Thus, the inflatable member 55 advantageously provides a deployable fixation means that can be activated and deactivated as desired by the clinician.

Although in the embodiment illustrated in FIGS. 2A and 2B the inflatable member 55 is shown near the distal end 38 and the electrode 40, and thus in the portion of the lead 10 implanted in the target branch vessel 30, in other embodiments, the inflatable member 55 may be positioned at any location on the distal portion 36. That is, the inflatable member 55 may be located at any location of the lead body 32 that will reside in the coronary sinus 18 or branch vessel 30 when the lead 10 is implanted.

Figure 3A:
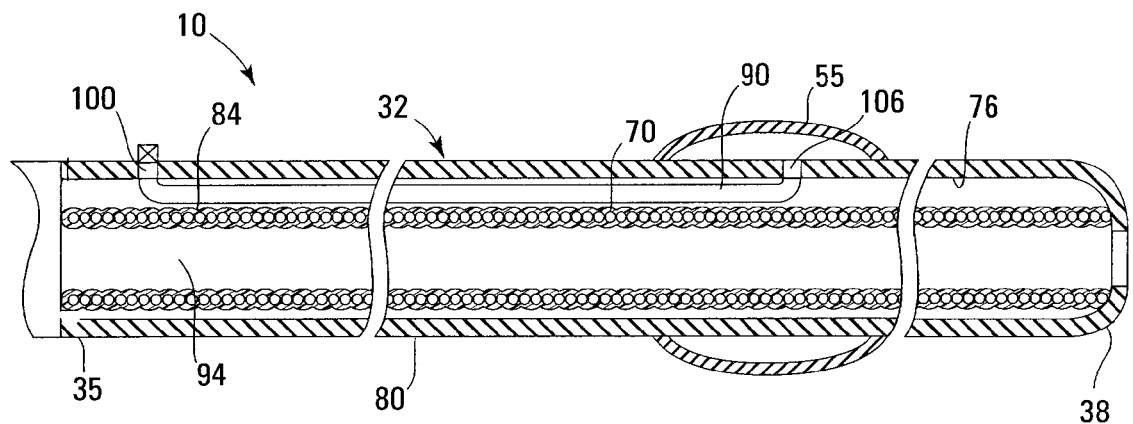
FIGS. 3A and 3B are cross-sectional views of a portion of a lead according to an embodiment of the present invention.
Figure 3B:
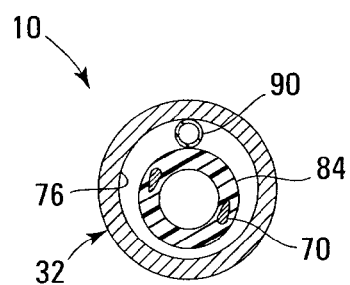

FIG. 3A is a cross-sectional side view of the lead 10 according to one embodiment of the present invention, and FIG. 3B is a cross-sectional end view of the lead 10. As shown, the lead 10 includes an electrically conductive member 70 extending from the proximal end 35 toward the distal end 38, and the lead body 32 includes an inner surface 76. In the illustrated embodiment, the conductive member 70 is in the form of an insulated wire coil. Thus, as can be seen in FIG. 3A, the lead body 32 provides an outer insulating layer 80, and the conductive member insulation forms an inner insulating layer 84 separated from the inner surface 76. The lead 10 further includes an inflation lumen 90 between the inner insulating layer 84 and the inner surface 76. As shown, the inflation lumen 90 is in the form of an elongate tubular member in fluid communication with the inflatable member 55, and operates to facilitate inflation of the inflatable member 55 using a suitable, biocompatible inflation media.

In the illustrated embodiment, the coiled conductive member 70 forms a primary lead lumen 94 which may facilitate lead delivery by receiving a stylet or guide wire as used in an over-the-wire delivery procedure. In another embodiment, the lead 10 may include a non-coiled conductive member 70 (i.e., a cable). In such embodiments, a separate lumen may be provided for lead delivery or other uses as deemed appropriate by the clinician. In various embodiments, other lumens may be provided for any uses desired by the clinician. In some embodiments, the lead 10 may include multiple conductive members, as are known for multi-electrode leads.

As further shown, the inflation lumen 90 is coupled to a portal 100 extending through the lead body 32 proximate the proximal end 35, and further extends through an orifice 106 in the lead body 32 to fluidly couple the portal 100 and the inflatable member 55. Thus, the inflatable member 55 can be inflated by introducing a fluid through the portal 100 until a desired degree of inflation of the inflatable member 55 is achieved.

Fluid or other inflation medium can be introduced into the inflation lumen 90 through the portal 100 using a syringe, indeflator or other appropriate introducing means known to in the art. The portal 100 may include a sealing mechanism (e.g., a seal such as a hemostasis valve seal) adapted to permit introduction of the syringe, indeflator, or other fluid introduction means, yet substantially prevent loss of fluid through the portal 100 after inflation of the inflatable member 55. In another embodiment, the portal 100 may be crimped or plugged to seal the portal 100 and prevent loss of inflation fluid there through. In another exemplary embodiment, the portal 100 may be self-sealing to maintain the inflation fluid within the inflation lumen 90 and the inflatable member 55. For example, the portal 100 may include a silicone plug. As is generally known, silicone tends to naturally seal itself upon being pierced. Other techniques and structures for sealing the portal 100 will be understood by those skilled in the art based on the foregoing.

Figure 4A:
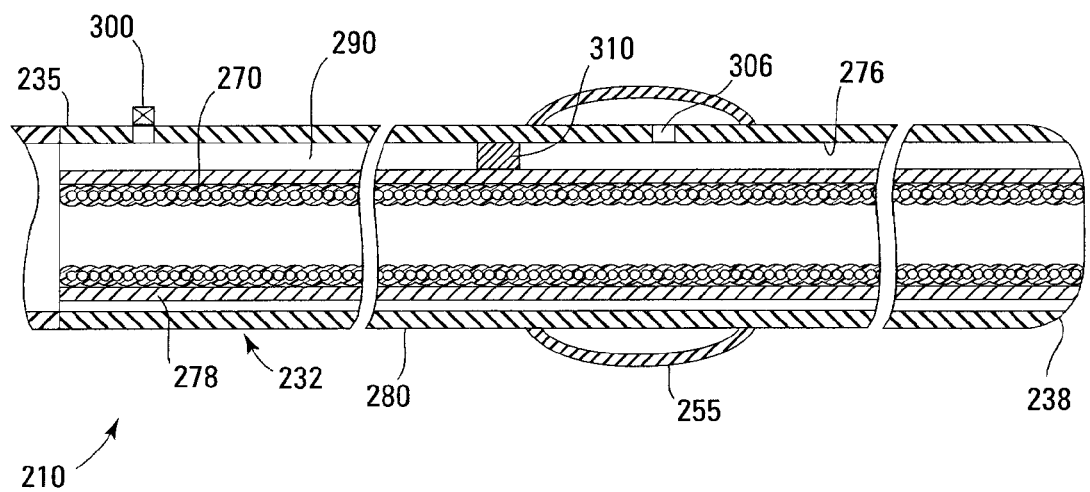
FIGS. 4A and 4B are cross-sectional views of a portion of a lead according to an alternative embodiment of the present invention.
Figure 4B:
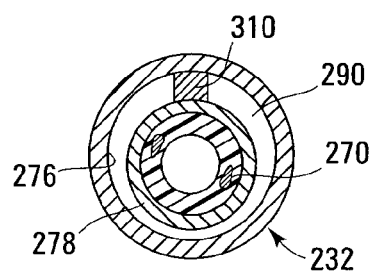

FIG. 4A is a cross-sectional side view of a lead 210 according to another embodiment of the present invention, and FIG. 4B is a cross-sectional end view of the lead 210. The lead 210 is overall similar to the lead 10, and includes a lead body 232 made of an electrically insulative material having a proximal end 235 and a distal end 238, and an inflatable member 255 on the lead body 232. As shown, the lead 210 includes an electrically conductive member 270 extending from the proximal end 235 toward the distal end 238, and the lead body 232 includes an inner surface 276. The lead 210 further includes a generally tubular, flexible inner insulating sheath 278 made of an electrically insulative material, e.g., polyurethane, disposed between the conductive member 270 and the inner surface 276 of the lead body 232. Thus, as can be seen in FIG. 4A, the lead body 232 provides an outer insulating layer 280, and the inner insulating sheath 278 forms an inner insulating layer separated from the inner surface 276 to define an inflation lumen 290 in fluid communication with the inflatable member 255. In another embodiment, an electrically insulative coating over the coiled conductive member 290 forms the inner insulating layer. Like the inflation lumen 90 of the lead 10, the annular inflation lumen 290 is configured to facilitate introduction of a fluid to inflate the inflatable member 255.

As further shown, the lead 210 further includes a portal 300 extending through the lead body 232 proximate the proximal end 235, and an orifice 306 extending through the lead body 232 to fluidly couple the inflatable member 255 and the inflation lumen 290. As with the lead 10, a fluid or other inflation medium can be introduced into the annular inflation lumen 290 using an syringe, indeflator or other appropriate introducing means known in the art through the portal 300, which may also include sealing features similar to those described above with respect to the lead 10.

As shown in FIG. 4B, in some embodiments, the lead 210 may include one or more optional spacer members 310 disposed between the inner insulation sheath 278 and the inner surface 276 of the lead body 232 to maintain separation therebetween, and thereby maintain the inflation lumen 290. In other embodiments, the lead 210 may include multiple spacer members 310. In one embodiment, elongated, circumferentially spaced ribs (not shown) may be provided extending longitudinally along the inner surface 276 of the lead body 232 or the inner insulation sheath 278, which may operate to separate those structures and provide channels (i.e., the spaces between adjacent ribs) which operate as the inflation lumen 290. Other structures and techniques for maintaining separation between the inner insulation sheath 278 and the inner surface 276 of the lead body will be apparent to those skilled in the art based on the foregoing.

The inflatable members 55, 255 described above may be made from any biocompatible or bio-absorbable material capable of maintaining sufficient hoop strength and burst pressure to provide fixation stability over a desired time duration and having sufficient softness to facilitate relatively unimpeded delivery of the respective lead. In various embodiments, the inflatable members 55 and/or 255 may be made substantially or entirely of silicone rubber, polyurethane, or polyether block amide. In one embodiment, the inflatable member is a silicone rubber membrane adhesively bonded to the outer surface of the lead body.

In an alternative embodiment, the inflatable member may be made from a semi-porous material selected to permit a controlled release of the inflation medium so as to allow deflation of the inflatable member over time. For example, in one such embodiment, it may be desirable for the inflatable member to supply a fixation force only for a limited duration, e.g., until tissue in-growth and fibrosis takes over as the primary fixation mechanism. In such a case, the inflatable member may be made from a semi-porous material configured to allow diffusion of the inflation medium into the bloodstream such that the inflatable member no longer provides a fixation force after, for example, two to four weeks. In yet another embodiment, a similar result can be achieved by making the inflatable member from a bio-absorbable material, as is known in the art.

The insulating materials (e.g., the bodies 32, 232 of the leads 10, 210, respectively) may be made from any electrically insulative materials suitable for transvenously deployed cardiac leads, whether now known or later developed. In one embodiment, the lead bodies 32, 232 and the inner insulating layer (i.e., the inner insulating layer 84 and the insulating sheath 278) are made substantially from polyurethane.

The inflatable members 55, 255 described above may be incorporated into any medical electrical leads sized and shaped for use in left ventricular stimulation. The lumen designs of the leads 10, 210 may facilitate incorporation of the inflatable members 55, 255 into smaller diameter lead sizes as compared to prior leads with inflatable balloon structures wherein the inflation lumen(s) were disposed within the thickness of the outer insulating layer of the lead body. That is, disposing the inflation lumen within the thickness of the lead body outer layer may require increasing the overall thickness of that layer, which in turn, results in a relatively larger diameter lead. Additionally, increasing the thickness of the outer insulating layer to accommodate the inflation lumen may increase the overall stiffness of the lead, which may in turn adversely affect transvenous delivery of the lead. In short, the inflation lumen configurations of the leads 10, 210 of the present invention may be better suited for left side leads which must be delivered through potentially tortuous venous anatomies.

The inflatable members 55, 255 described herein may be inflated using any biocompatible fluid, including without limitation, air, a saline solution, or any other biocompatible gas or liquid media.

Figure 5A:
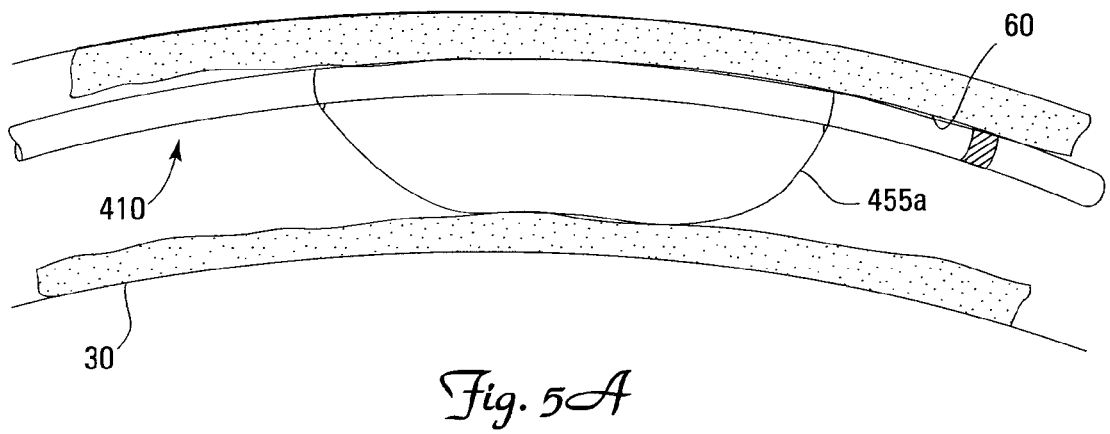
FIGS. 5A and 5B illustrate portions of leads including inflatable fixation members according to additional embodiments of the present invention.
Figure 5B:
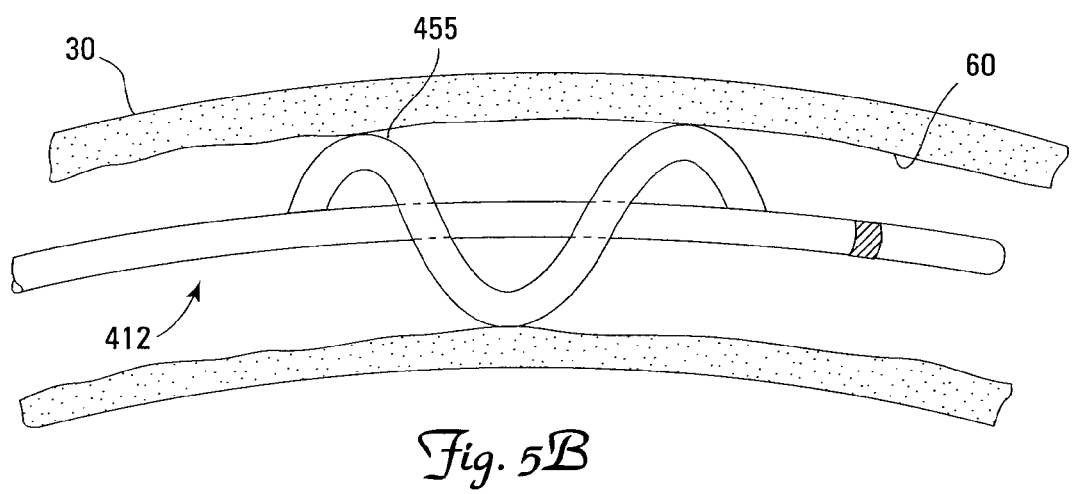

FIGS. 5A and 5B illustrate portions of leads 410, 412 respectively, according to yet additional embodiments of the present invention. The leads 410, 412 can in many respects be substantially the same as or identical to any of the leads described above, the exceptions being in the inflatable member configurations. As shown in FIG. 5A, the lead 410 includes an inflatable member 455 that extends only partially around the lead body. In one embodiment, for example, the inflatable member 455 extends between about 90° and about 270° about the lead body. By the illustrated configuration, when inflated, the inflatable member 455 can advantageously cause the lead electrode to be biased toward the inner surface 60 of the target branch vessel 30 in which the distal end of the lead 410 is implanted. Accordingly, the inflatable member 455 operates to secure the lead 410 in place and also to improve electrode contact with the vessel tissue. As shown in FIG. 5B, the lead 412 includes an inflatable member 455 that is disposed about the lead body in a generally helical configuration. It will be appreciated that other inflatable member shapes and configurations may be utilized within the scope of the present invention.

In the illustrated embodiments described above, the respective leads include a single inflatable fixation member, e.g., the inflatable members 55, 255, and 455. In other embodiments, a plurality of inflatable members are provided. For example, in one embodiment, the lead may include two or more inflatable members located along the lead body such that they will be positioned in the target branch vessel in which the lead distal end is implanted. In other embodiments, the lead may include one inflatable member at a location such that it can be positioned in the target branch vessel, and another inflatable member positioned in the coronary sinus 18 (see FIG. 1). In such an embodiment, the inflatable member positioned in the coronary sinus 18 may provide enhanced stability and fixation strength during the implantation procedure (e.g., as during retraction of the guide wire in an over-the-wire implantation, as is known). Other combinations of inflatable fixation members will be understood by those skilled in the art based on the foregoing.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A medical electrical lead comprising:
an elongate lead body having a proximal end, a distal end, an outer surface, and an inner surface, the body being made from an electrically insulative material and dimensioned such that the distal end can be implanted in a coronary sinus or coronary vein;
an inflatable member disposed on the outer surface of the body between the proximal and distal ends, the inflatable member adapted to assume a deflated state and an inflated state in which the inflatable member is adapted to impart a radial force on and frictionally engage a surface of the coronary sinus or coronary vein for fixation of the distal end therein, the inflatable member including a resilient membrane attached to and extending partially circumferentially around a portion of the lead body;
a conductive member extending from at least the proximal end toward the distal end of the body;
an inner insulating layer disposed between the conductive member and the inner surface of the body and extending from the proximal end toward the distal end;
an inflation lumen between the inner insulating layer and the inner surface of the body in fluid communication with the inflatable member; and
an electrode on the body electrically coupled to the conductive member.

2. The lead of claim 1 wherein the resilient membrane extends from about 90 degrees to about 270 degrees around the portion of the lead body, and wherein in the inflated state the inflatable member is adapted to bias the electrode toward the surface of the coronary sinus or coronary vein.

3. The lead of claim 1 wherein the inflatable member includes a resilient membrane attached to the outer surface of the body and extending around a portion of the body in a generally helical configuration.

4. The lead of claim 1 and further comprising a portal extending through the body proximate the proximal end, the portal adapted to facilitate introduction of a fluid into the inflation lumen.

5. The lead of claim 4 and further comprising a sealing feature coupled to the portal to substantially prevent loss of fluid through the portal.

6. The lead of claim 4 and further comprising an orifice extending through the lead body to fluidly couple the inflatable member and the inflation lumen.

7. The lead of claim 1 wherein the inflatable member is made substantially from a material selected from the group consisting of silicone, polyurethane, polyether block amide, and a bio-absorbable polymer.

8. The lead of claim 1 wherein the lumen is an elongate tubular member coupled to a portal located proximate the proximal end of the lead body.

9. A medical electrical lead comprising:
an elongate lead body having a proximal end, a distal end, an outer surface, and an inner surface, the body being made from an electrically insulative material and dimensioned such that the distal end can be implanted in a coronary sinus or coronary vein;
an inflatable member disposed on the outer surface of the body between the proximal and distal ends, the inflatable member adapted to assume a deflated state and an inflated state in which the inflatable member is adapted to impart a radial force on and frictionally engage a surface of the coronary sinus or coronary vein for fixation of the distal end therein;
a conductive member extending from at least the proximal end toward the distal end of the body, the conductive member including an insulative coating, wherein separation between the insulative coating and the inner surface of the body defines an inflation lumen in fluid communication with the inflatable member; and
an electrode on the body electrically coupled to the conductive member.

10. The lead of claim 9 and further comprising at least one spacing member disposed between the insulative coating and the inner surface of the lead body, the spacing member adapted to maintain the separation between the insulative coating and the inner surface of the body.

11. The lead of claim 9 and further comprising a portal extending through the body proximate the proximal end, the portal adapted to facilitate introduction of a fluid into the inflation lumen.

12. The lead of claim 11 and further comprising a sealing feature coupled to the portal to substantially prevent loss of fluid through the portal.

13. The lead of claim 11 and further comprising an orifice extending through the lead body to fluidly couple the inflatable member and the inflation lumen.

14. A medical electrical lead comprising:
an elongate lead body having a proximal end, a distal end, an outer surface, and an inner surface, the body being made from an electrically insulative material and dimensioned such that the distal end can be implanted in a coronary sinus or coronary vein;
an inflatable member disposed on the outer surface of the body between the proximal and distal ends, the inflatable member adapted to assume a deflated state and an inflated state in which the inflatable member is adapted to impart a radial force on and frictionally engage a surface of the coronary sinus or coronary vein for fixation of the distal end therein;

a conductive member extending from at least the proximal end toward the distal end of the body;

a generally tubular, flexible sheath made of an electrically insulative material disposed between the conductive member and the inner surface of the body, wherein separation between the sheath and the inner surface of the body defines an inflation lumen in fluid communication with the inflatable member; and an electrode on the body electrically coupled to the conductive member.

15. The lead of claim 14 and further comprising at least one spacer member disposed between the sheath and the inner surface of the lead body, the spacer member adapted to maintain the separation between the sheath and the inner surface of the body.

16. The lead of claim 14 and further comprising a portal extending through the body proximate the proximal end, the portal adapted to facilitate introduction of a fluid into the inflation lumen.

17. The lead of claim 16 and further comprising a sealing feature coupled to the portal to substantially prevent loss of fluid through the portal.

18. The lead of claim 17 and further comprising an orifice extending through the lead body to fluidly couple the inflatable member and the inflation lumen.

19. A medical electrical lead comprising:

an elongate lead body having a proximal end, a distal end, an outer surface, and an inner surface, the body being made from an electrically insulative material and dimensioned such that the distal end can be implanted in a coronary sinus or coronary vein;

an inflatable member disposed on the outer surface of the body between the proximal and distal ends, the inflatable member adapted to assume a deflated state and an inflated state in which the inflatable member is adapted to impart a radial force on and frictionally engage a surface of the coronary sinus or coronary vein for fixation of the distal end therein;

a conductive member extending from at least the proximal end toward the distal end of the body;

an inner insulating layer disposed between the conductive member and the inner surface of the body and extending from the proximal end toward the distal end;

an inflation lumen between the inner insulating layer and the inner surface of the body in fluid communication with the inflatable member;

a portal extending through the body proximate the proximal end, the portal adapted to facilitate introduction of a fluid into the inflation lumen;

a sealing feature coupled to the portal to substantially prevent loss of fluid through the portal; and an electrode on the body electrically coupled to the conductive member.

* * * * *